United States Patent [19]
Redlich et al.

[11] Patent Number: 5,648,086
[45] Date of Patent: Jul. 15, 1997

[54] STABLE SOLID FORM ANTIMICROBIAL COMPOSITIONS COMPRISING 3-ISOTHIAZOLONES

[75] Inventors: George Harvey Redlich, Norristown; Gary Lewis Willingham, Glenside; John Steven Chapman, Ambler, all of Pa.

[73] Assignee: Rohm and Haas Company, Philadelphia, Pa.

[21] Appl. No.: 471,888

[22] Filed: Jun. 6, 1995

Related U.S. Application Data

[60] Division of Ser. No. 784,852, Oct. 30, 1991, which is a continuation-in-part of Ser. No. 625,265, Dec. 10, 1990, abandoned.

[51] Int. Cl.⁶ .......................... A01N 25/08; A61K 31/425
[52] U.S. Cl. .............................. 424/409; 514/372
[58] Field of Search ................ 424/409; 514/372

[56] References Cited

U.S. PATENT DOCUMENTS

| 4,542,169 | 9/1985 | Costerton | 523/121 |
| 4,552,591 | 11/1985 | Millar | 106/18 |

FOREIGN PATENT DOCUMENTS

| 106562 | 4/1984 | European Pat. Off. . |
| 106563 | 4/1984 | European Pat. Off. . |

*Primary Examiner*—Kimberly Jordan
*Attorney, Agent, or Firm*—Julie J. L. Cheng

[57] ABSTRACT

Solid, stable forms of 3-isothiazolone microbicidal compositions and articles using a carrier which functions to stabilize the microbicide against chemical decomposition at room temperature and at applications temperature.

4 Claims, No Drawings

STABLE SOLID FORM ANTIMICROBIAL COMPOSITIONS COMPRISING 3-ISOTHIAZOLONES

This is a divisional of application Ser. No. 07/784,852, filed Oct. 30, 1991, which is a continuation-in-part of Ser. No. 07/625,265, filed Dec. 10, 1990, now abandoned.

I. BACKGROUND OF THE INVENTION

A. Field of the Invention

This invention relates to stable, solid form antimicrobial compositions comprising 3-isothiazolones.

B. Description of the Prior Art

U.S. Pat. No. 4,552,591, Millar, shows 3-isothiazolones absorbed on particulate solid (diatomaceous earth) for oil field fluid applications.

European Patent Application 106,562 of Apr. 25, 1984 shows similar solid formulations to Millar.

European Patent Application 106,563 of Apr. 25, 1984 shows stable, non-irritating, slow-release compositions containing 3-isothiazolones, an inert filler, and a high-melting solid, wax-like binder.

European Patent Application publication 0147223 of Jul. 3, 1985, shows the combination of organic hydroperoxides with organic biocides giving enhanced activity. Among the biocides listed is 3-isothiazolone.

U.S. Pat. No. 4,975,109 discloses combinations of oxidants and microbicides, among which are 3-isothiazolones, showing enhanced activity.

II. SUMMARY OF INVENTION

It is an object of the present invention to provide 3-isothiazolones in solid, stable form. Another object is to provide solid form 3-isothiazolone microbicide compositions which are safe to handle, convenient to use and stable.

A further object is to provide salt-free, "stabilizer-free," 3-isothiazolone microbicide compositions which are solid form.

These objects and others which will become apparent from the following disclosure are achieved by the present invention which comprises in one aspect antimicrobial compositions comprising (A) a 3-isothiazolone compound, and (B) a carrier which is solid at room temperature, said carrier functioning to stabilize said 3-isothiazolone against chemical decomposition at room temperature and at applications temperature, said composition being solid at room temperature.

In another aspect the invention comprises such compositions in the form of powder, bar, pellet, tablet, cast sheet or granules.

In another aspect the invention comprises 3-isothiazolone microbicide compositions which are solid form.

III. DETAILED DESCRIPTION OF THE INVENTION

The 3-isothiazolones used in the invention are well known microbicides and are usually of the formula

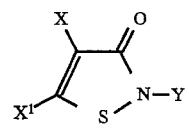

wherein

Y is selected from the group consisting of hydrogen; alkyl or substituted alkyl of 1 to 18 carbon atoms; unsubstituted or halogen- substituted alkenyl or alkynyl of 2 to 8 carbon atoms; cycloalkyl or substituted cycloalkyl of 3 to 12 carbon atoms; aralkyl or halogen-, lower alkyl-, or lower alkoxy-substituted aralkyl of up to 10 carbon atoms; and aryl, halogen-, lower alkyl-, or lower alkoxy-substituted aryl of up to 10 carbon atoms; and X and $X^1$ are independently selected from the group consisting of hydrogen, halogen, and $(C_1-C_4)$alkyl.

The carrier functions both as an agent to impart solidity and to impart stability. Many conventional carriers which would impart solidity do not also impart chemical stability, and those are not included in this invention.

We have discovered a special class of carriers which have this dual function. We prefer those which are selected from the group consisting of polysaccharide polymers, cellulose polymers, derivatized cellulose polymers, polymers and copolymers of ethylene oxide and propylene oxide, polyurethane polymers having alternating hydrophobic and hydrophilic moieties, poly(maleic anhydride/methyl vinyl ether), polymethacrylic acid, and naphthalene formaldehyde condensates.

Usually the carriers are water soluble, and this is preferred.

Any suitable ratio can be used, but we prefer from about 0.1:99.9 to about 90:10 by weight, and more preferably from about 1.5:98.5 to about 25:75.

A special utility wherein no salt stabilizer is used is surprising and unexpected because salts are generally used with most commercial 3-isothiazolones to stabilize them. Compositions free of the presence of salt or stabilizer (other than the carrier itself) are especially useful.

If desired, the composition can also include one or more additives selected from the group consisting of deodorant, dye, sequestrant, fragrance, tableting aid, surfactant, additional antimicrobial compound, dispersant, antisettling agent, and excipient.

The use of certain additional antimicrobial compounds has advantages in increasing speed of kill, but preblending such additional antimicrobial compounds with the isothiazolones causes degradation of the isothiazolones. The use of the solid carrier for combinations of antimicrobial compounds allows for a delivery system which avoids the problems associated with premixing antimicrobials. This is particularly applicable to combinations of 3-isothiazolones with additional antimicrobials from the peroxide class such as t-butyl hydroperoxide, dilauroyl peroxide, and hydrogen peroxide, and other classes such as peracids, peroxycarbonates, peroxydicarbonates, perborates, peracids, perchlorides, and the like. Preferred ratios are about 1:1 to 1:200, more preferably 1:10 to 1:20, isothiazolone to additional antimicrobial.

Usually the compositions and articles of the invention are stable at room temperature and for at least 3 days at 55° C. as measured by retention of 3-isothiazolone compound.

The invention can be in the form of a powder, bar, pellet, tablet, cast sheet or granules.

The composition can be prepared by mixing a solution of the 3-isothiazolone in an organic solvent with the carrier and thereafter removing said solvent; mixing the isothiazolone and the carrier in the presence of water to form a slurry or a solution and thereafter removing the water by evaporation or spray drying; melt blending the 3-isothiazolone and the carrier and thereafter molding or extruding said composition into a desired shape; or other suitable means.

The invention includes an improved method of delivering 3-isothiazolone antimicrobial compound to a locus.

The following examples are presented to illustrate a few embodiments of the invention. All parts and percentages are by weight unless otherwise indicated.

EXAMPLES

EXAMPLE 1

8.6 grams of molten polyurethane polymer with alternating hydrophobic and hydrophilic blocks (QR 708, Rohm and Haas), was blended with 1.4 grams of melted 3-isothiazolone (4:1 blend of 5-Cl-2- methyl-3-isothiazolone and 2-methyl-3-isothiazolone), by hand stirring. The molten material was spread out on the sides of the vessel to allow cooling to occur. The hardened product was then broken into flake-like particles.

EXAMPLE 2

In a manner similar to Example 1 18.2 g of the polyurethane and 0.22 g of oxyfluorfen were melted together on a steam bath. 1.62 g of molten isothiazolone was then blended in via hand stirring. Analysis of the product gave the following:

| | |
|---|---|
| oxyfluorfen | 0.93% |
| 5-Cl-2-methyl-3 isothiazolone | 7.4% |
| 2-methyl-3-isothiazolone | 1.3% |

An analogous sample yielded the following heat aging results:

| | oxyfluorfen (%) | 5-Cl-2-methyl-3-isothiazolone (%) | 2-methyl-3-isothiazolone (%) |
|---|---|---|---|
| 0 Time | 0.34 | 6.2 | 1.3 |
| 2 wk/55° C. | 0.33 | 5.9 | 1.3 |
| 4 wk/55° C. | 0.35 | 3.3 | 1.3 |

Normally the unstabilized lifetime of 5-chloro-2-methyl-3-isothiazolone at 55° C. is 2–3 days.

EXAMPLE 3

Following the procedure of Example 1 except using polyethylene oxides of molecular weights ranging from 1450–20,000, (Carbowax, Union Carbide) in place of the polyurethane, the 2-n-octyl-3-isothiazolone was blended with the molten polyethylene oxides to yield solid formulations with AI between 9.5 and 12%.

EXAMPLE 4

Methylene chloride was used to swell/dissolve the polyurethane (QR-735, Rohm and Haas) so that the blending could be done at a lower temperature, 35° C. On cooling to RT the material hardened and the residual solvent was removed by evaporation.

EXAMPLE 5

Polyethylene oxide polymer (Polyox WSR 1105, Union Carbide), was suspended in an acetone solution of the 4:1 blend of 5-chloro-2-methyl-3-isothiazolone and 2-methyl-3-isothiazolone placed onto a Roto-Vap and the acetone stripped off. A product containing 4% AI was prepared. A sample was stored at 55° C. for three days, which retained >75% AI. A similar sample, prepared on sodium sulfate retained <25% AI under the same conditions.

EXAMPLE 6

Additional examples of water soluble/swellable polymers were prepared according to the process in Example 5, and are shown in Table I. All these retained >75% AI upon storage at 55° C. for three days.

Table I

Additional Examples of Solid Carriers Which Display Stabilizing Function

Polysaccharides
  Potassium Alginate
  Karaya Gum
  Gum Tragacanth
Cellulosics
  Hydroxypropyl methylcellulose (Methocel K4M, Dow)
  Methylcellullose (Methocel A15LV, Dow)
  Carboxymethyl cellulose (Ac-Di Sol)
  Cellulose (Avicel, FMC)
Soluble Synthetic Polymers
  p(maleic anhydride/methyl vinyl ether) (Gantrez AN-119 GAF)
  p(ethyleneoxide) (Polyox WRS 1105 & N-10, Union Carbide)
  p(methacrylic acid) (Tamol 731, Rohm and Haas)
  naphthalene sulfonate condensates (Tamol SN, Rohm & Haas Morwet EFW, DeSoto)

EXAMPLES 7–10

These examples illustrate different solid formulations of 3-isothiazolones and additional antimicrobial compounds.

EXAMPLE 7

This example illustrates the blending of a 3-isothiazolone with an additional antimicrobial compound in the molten state. To 9.58 g of the molten polyurethane polymer used in Example I were blended 0.46 g of 70% t-butyl hydroperoxide and 0.20 g of molten 3-isothiazolone (a 3:1 mixture of 5-chloro-2-methyl-3-isothiazolone and 2-methyl-3-isothiazolone) by hand stirring. The molten material was spread out on the sides of the vessel to allow cooling to occur. The hardened product was then broken into flake-like particles.

EXAMPLE 8

Methanol was used to swell/dissolve the polyurethane polymer (QR 708, Rohm and Haas) so that blending could be done at a lower temperature than Example 1. To 9.5 g of the polyurethane polymer used in Example I were added 20 g of methanol and the material allowed to swell. To this swelled material were added 0.30 g of benzoyl peroxide and 0.20 g of the 3:1 mixture of 5-chloro-2-methyl-3-isothiazolone and 2-methyl-3-isothiazolone. After mixing, the solvent was allowed to evaporate. The hardened product was then broken up into flake-like particles.

EXAMPLE 9

This example illustrates the use of co-solvents to swell/dissolve the polyurethane polymer used in Example I. A 1:1 blend of methylene chloride and methanol was used to swell the polyurethane polymer. To 9.7 g of polymer at 35 ° C. were added 20 g of the co-solvent mixture. Once the polymer had swelled, 0.2 g of dilauroyl peroxide and 0.2 g of the 3:1 mixture of 5-chloro-2-methyl-3-isothiazolone and 2-methyl-3-isothiazolone were added. After blending the ingredients, the solvent was allowed to evaporate. The resulting solid was broken into flakes.

EXAMPLE 10

To 9.08 g of molten polyurethane polymer used in Example 1 were blended 0.71 g of 70% t-butyl hydroperoxide and 0.21 g of a 3:1 mixture of 5-chloro-2-methyl-4-isothiazolin-3-one and 2-methyl -4-isothiazolin-3-one, 15% active ingredient and 15% magnesium nitrate stabilizer (Kathon 886, Rohm and Haas), by hand stirring. The molten material was spread out on the sides of the vessel to allow cooling to occur. The hardened material was then broken into flake-like particles.

EXAMPLE 11

The particles made according to Example 10 were dispersed in water and dissolved in bacterial growth medium at 37° C. with shaking. The bacterial growth medium was minimal salts and glucose media with *Pseudomonas aeruginosa* (ATCC #15442), with $2\times10^7$ colony-forming units/mi. The number of organisms killed increased by a factor of 10,000 as compared to using equal weights of either 5-chloro-2-methyl-4-isothiazolin-3-one alone or t-butyl hydroperoxide alone.

While the invention has been described with reference to specific examples and applications, other modifications and uses for the invention will be apparent to those skilled in the art without departing from the spirit and scope of the invention defined in the appended claims.

We claim:

1. Antimicrobial composition comprising (A) a 3-isothiazolone compound, and (B) a water-soluble polymeric carrier which is solid at room temperature, said carrier functioning to stabilize said 3-isothiazolone against chemical decomposition at room temperature and at applications temperature, said composition being solid at room temperature further including one or more additives selected from the group consisting of deodorant, dye fragrance, sequestrant, tableting aid, surfactant, additional antimicrobial compound, dispersant, antisettling agent, and excipient.

2. Composition according to claim 1 including an additional antimicrobial compound selected from the group consisting of organic peroxides, hydrogen peroxide, peracids, peroxycarbonates, peroxydicarbonates, perborates, peracids and perchlorides.

3. Composition according to claim 2 wherein said additional antimicrobial is selected from the group consisting of t-butyl hydroperoxide, lauryl peroxide, and hydrogen peroxide.

4. Method of stabilizing a 3-isothiazolone against chemical decomposition comprising combining the 3-isothiazolone with a water soluble polymeric carrier to impart solidity and stability to the 3-isothiazolone, said carrier selected from the group consisting of polysaccharide polymers, cellulose polymers, derivatized cellulose polymers, polymers and copolymers of ethylene oxide and propylene oxide, polyurethane polymers having alternating hydrophobic and hydrophylic moieties, poly(maleic anhydride/methyl vinyl ether), polymethacrylic acid, and naphthalene formaldehyde condensates.

* * * * *